United States Patent
Yen et al.

(10) Patent No.: US 8,593,052 B1
(45) Date of Patent: Nov. 26, 2013

(54) MICROELECTRODE ARRAY AND METHOD FOR MODIFYING CARBON NANOTUBE ELECTRODE INTERFACE OF THE SAME ARRAY

(75) Inventors: Shiang-Jie Yen, Penghu (TW); Huan-Chieh Su, Changhua (TW); Tri-Rung Yew, Hsinchu (TW); Yen-Chung Chang, Hsinchu (TW); Wei-Lun Hsu, Taipei (TW); Shih-Rung Yeh, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 1015 days.

(21) Appl. No.: 12/638,429

(22) Filed: Dec. 15, 2009

(51) Int. Cl.
- *H01J 1/63* (2006.01)
- *H01J 63/04* (2006.01)
- *H01J 17/49* (2012.01)

(52) U.S. Cl.
USPC ........... 313/495; 313/496; 313/497; 313/498; 313/499; 313/309; 445/1; 445/254; 445/25

(58) Field of Classification Search
None
See application file for complete search history.

(56) References Cited

U.S. PATENT DOCUMENTS

| | | | |
|---|---|---|---|
| 7,008,758 B2 * | 3/2006 | Park et al. | 430/325 |
| 2004/0101634 A1 * | 5/2004 | Park et al. | 427/558 |
| 2011/0177493 A1 * | 7/2011 | Lu | 435/5 |

OTHER PUBLICATIONS

Ricci, David, "Carbon nanotubes for neural interfaces," presented a tNano-electronics and photonics of The Electrochemical Society, Oct. 14, 2008, website: http://www.electrochem.org/meetings/scheduler/programs.aspx?m_d=2.

Keffer et al., "Carbon nanotube coating improves neuronal recordings," Nature Nanotechnology, 2008, pp. 434-439, vol. 3, Published online: Jun. 29, 2008.

Ke Wang, "Neural Stimulation with a Carbon Nanotube Microelectrode Array," Nano Letters, 2006, pp. 2043-2048, vol. 6, No. 9.

Lovat et al, "Carbon Nanotube Substrates Boost Neuronal Electrical Signaling," Nano Letters, 2005, pp. 1107-1110, vol. 5, No. 6.

Ben-Jacob et al., "Carbon nanotube micro-electrodes for neuronal interfacing," Journal of Materials Chemistry, 2008, pp. 5181-5186, vol. 18.

* cited by examiner

*Primary Examiner* — Natalie Walford
(74) *Attorney, Agent, or Firm* — Muncy, Geissler, Olds & Lowe, PLLC

(57) ABSTRACT

The present invention discloses a method for modifying a carbon nanotube electrode interface, which modifies carbon nanotubes used as a neuron-electrode interface by performing three stages of modifications and comprises the steps of: carboxylating carbon nanotubes to provide carboxyl functional groups and improve the hydrophilicity of the carbon nanotubes; acyl-chlorinating the carboxylated carbon nanotubes to replace the hydroxyl functional groups of the carboxyl functional groups with chlorine atoms; and aminating the acyl-chlorinated carbon nanotubes to replace the chlorine atoms with a derivative having amine functional groups at the terminal thereof. The modified carbon nanotubes used as the neuron-electrode interface has lower impedance and higher adherence to nerve cells. Thus is improved the quality of neural signal measurement. The present invention also discloses a microelectrode array, wherein the neuron-electrode interface uses carbon nanotubes modified according to the method of the present invention.

10 Claims, 6 Drawing Sheets

MICROELECTRODE ARRAY AND METHOD FOR MODIFYING CARBON NANOTUBE ELECTRODE INTERFACE OF THE SAME ARRAY

FIELD OF THE INVENTION

The present invention relates to a method for modifying a carbon nanotube electrode interface, particularly to a method for modifying a carbon nanotube electrode interface, which can increase the affinity of neuron cells to the electrodes and improve the quality of neural signals. The present invention also relates to a microelectrode array using the carbon nanotube modified by the abovementioned method.

BACKGROUND OF THE INVENTION

Since a planar multi-electrode array was proposed to study the transmission mechanism of neural signals in 1972, microelectrode arrays have been extensively used in the biomedical engineering. The brain or a neural network is a complicated network consisting of many neurons interconnecting each other. Understanding the operation of the neural network is very important to diagnose or treat neural diseases or fabricate neural prostheses. A probe can easily puncture the skin to detect the electrophysiological signals in vivo. A probe may also function as an intermediary between analog physiological signals and digital signal analysis.

FIG. 1 shows a microelectrode array 10 for detecting neural signals. The microelectrode array 10 comprises a base 11 and a plurality of probes 12 connected to the base 11. Each probe 12 has a plurality of electrodes 13. For example, each probe 12 has four electrodes 13 in FIG. 1. Each electrode 13 is electrically connected to a metal pad 15 of the base 11 via a wire 14. Each wire 14 is insulated from the environment. The neural signals detected by the electrode 13 is transmitted to the base 11 via the wire 14 and then processed by the succeeding devices.

Carbon nanotube, which was found by S. Iijima in 1991, has a superior electric conductivity because of its special structure. Thus, carbon nanotube has been widely used in the nanometric electronic elements. The electrode interfaces of the conventional probes are usually made of a metal having better biocompatibility, such as gold, platinum, titanium, or platinum black. However, the interfacial resistance of the metal electrode increases when the size of a metal electrode is reduced to a very small scale. Thus, the efficiency of the entire circuit decreases.

Carbon nanotube has very large surface area, high electrical conductivity, better physicochemical properties, better chemical inertness and better biocompatibility. Therefore, more and more applications use carbon nanotube as the interface of neural electrodes, for example, "Carbon Nanotubes for Neural Interfaces" by David Ricci; "Carbon Nanotube Coating Improves Neuronal Recording" by Edward, et al., Nature Nanotech., 2008; "Neural Stimulation with a Carbon Nanotube Microelectrode Array" by Ke Wang, Nano Lett., 2006; "Carbon Nanotube Substrates Boost Neuronal Electrical Signaling" by Viviana Lovat, et al., Nano Lett., 2005; "Carbon Nanotube Micro-Electrodes for Neuronal Interfacing" by E. Ben-Jacob, et al., J. Mater. Chem., 2008.

The abovementioned technologies are only the rudimentary carbon nanotube applications in the neural electrode interface. The present invention further modifies the carbon nanotube electrode interface and forms the functional groups, which neuron cells prefer to adhere to. Therefore, neural signals were enhanced with the use of this modified CNT electrode.

SUMMARY OF THE INVENTION

One objective of the present invention is to provide a method for modifying a carbon nanotube electrode interface to improve the adherence of neuron cells, decrease the impedance between the electrode interface and the biological tissues, and promote the signal intensity and quality of measurement.

To achieve the abovementioned objective, the present invention proposes a method for modifying a carbon nanotube electrode interface, which modifies carbon nanotubes used as a neuron-electrode interface by performing three stages of modifications, including a carboxylation process, an acyl-chlorination process, and an amination process. Surfaces of the carbon nanotubes have carboxyl functional groups after the carboxylation process. Next, the hydroxyl functional groups of the carboxyl functional groups are replaced by chlorine atoms of thionyl chloride in the acyl-chlorination process. Next, the amination process replaces the chlorine atoms with the amine functional groups, which were favored by neuron cells.

In one embodiment, the carbon nanotubes of the neuron-electrode interface are modified directly. In one embodiment, the carboxylation process is carried out by a $H_2O$ plasma process. In one embodiment, the acyl-chlorination and amination are performed in a reflux system.

The present invention also provides a microelectrode array, which comprises a base and at least one probe connected to the base. Each probe has at least one electrode. The electrode uses the carbon nanotubes as the neuron-electrode interface thereof, and the carbon nanotubes is modified with the abovementioned method.

Below, the technical contents of the present invention are described in detail with the embodiments and drawings.

DETAILED DESCRIPTION OF THE PREFERRED EMBODIMENTS

The present invention proposes a method for modifying a carbon nanotube electrode interface, which modifies carbon nanotubes used as a neuron-electrode interface to increase the adherence of neuron cells to the carbon nanotube electrode interface, improve the biocompatibility of neuronal, and promote the quality of electrophysiological signals.

Figure 1:
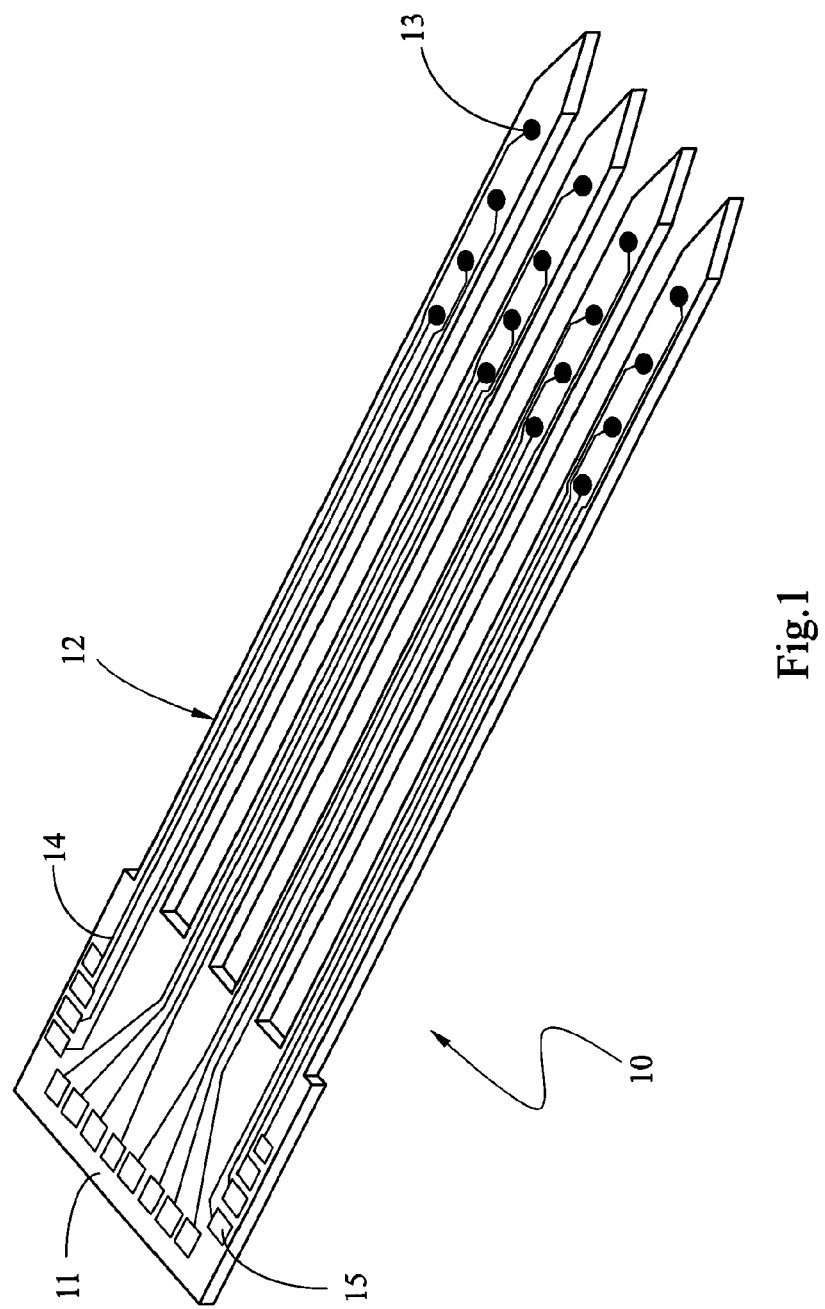
FIG. 1 is a diagram schematically showing a microelectrode array for detecting neural signals according to the present invention.
Figure 2:
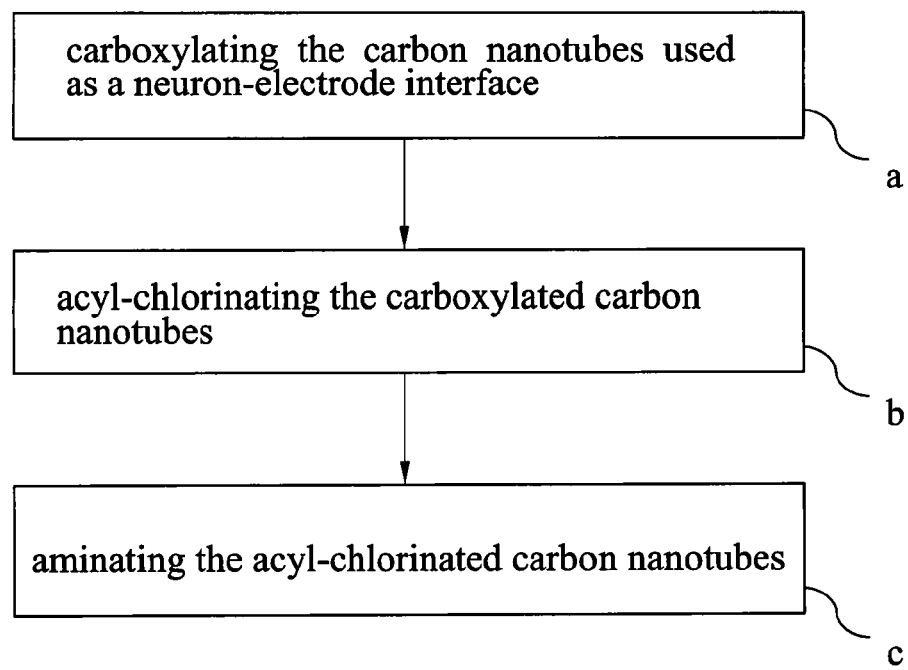
FIG. 2 is a flowchart of a method for modifying a carbon nanotube electrode interface according to the present invention.
Figure 3:
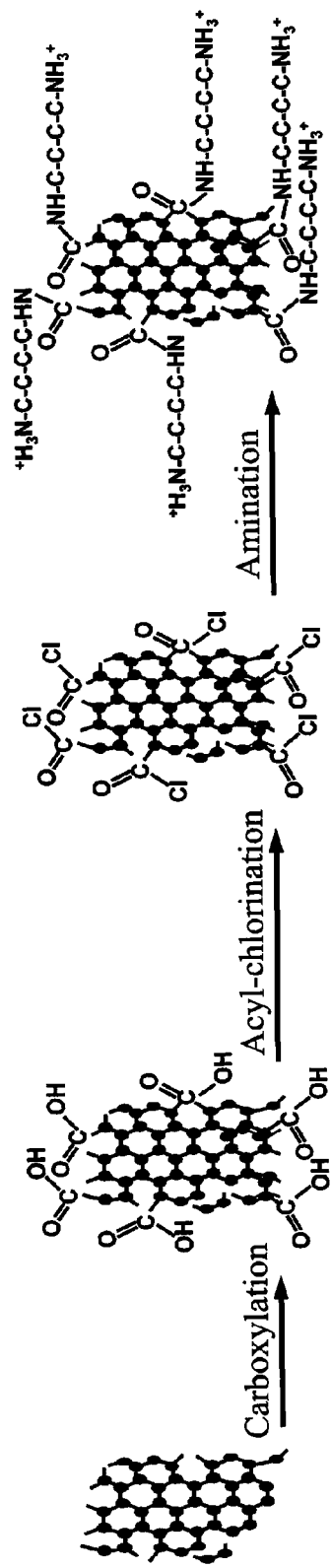
FIG. 3 is a diagram schematically showing a method for modifying a carbon nanotube electrode interface according to the present invention.

Refer to FIG. 2 and FIG. 3 respectively a flowchart and a schematic diagram of a method for modifying a carbon nanotube electrode interface according to the present invention.

The method of the present invention comprises a carboxylation process (Step a), an acyl-chlorination process (Step b) and an amination process (Step c).

In the Step a, the carbon nanotubes are carboxylated to form a plurality of carboxyl functional groups "O=C—OH" on surfaces of the carbon nanotubes (as shown in FIG. 3) to improve the hydrophilicity of the carbon nanotubes. In one embodiment, a microelectrode array used the carbon nanotubes as the neuron-electrode interface is washed with deionized water and then dried. Next, the microelectrode array is processed with a $H_2O$ plasma to generate the carboxyl functional groups "O=C—OH" on the carbon nanotubes. The $H_2O$ plasma process is performed at a temperature of 25-150° C., under a pressure of 1-100 Ton, with a power of 25-100 W, for 10-300 seconds. The amount of the carboxyl functional groups correlates with the processing time of the $H_2O$ plasma. If the processing time is too short, it results in insufficient carboxyl functional groups. If the processing time is too long, the carbon nanotubes will be damaged.

In other embodiment, the carboxylation process is carried out by an $O_2$ plasma process or via immersing the carbon nanotubes into an acidic solution at an ambient temperature. The acidic solutions include but are not limited to nitric acid ($HNO_3$), sulfuric acid ($H_2SO_4$), and hydrogen peroxide ($H_2O_2$).

In the Step b, the carboxylated carbon nanotubes are further acyl-chlorinated to replace the hydroxyl functional groups of the carboxyl functional groups with chlorine atoms and form "O=C—Cl" functional groups. In the acyl-chlorination process, the carboxylated carbon nanotubes react with thionyl chloride ($SOCl_2$), phosphorus trichloride ($PCl_3$), phosphorus pentachloride ($PCl_5$), Oxalyl dichloride ($COCl)_2$, or cyanuric chloride ($C_3N_3Cl_3$), and the hydroxyl functional groups thereof are thus replaced by the chlorine atoms.

In one embodiment, the acyl-chlorination process is carried out with a chemical synthesis method, wherein the carboxylated carbon nanotubes react with the thionyl chloride in a reflux system, and the reaction formula thereof is expressed by Formula (I).

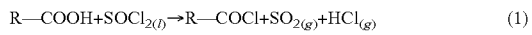

$$R\text{—}COOH+SOCl_{2(l)} \rightarrow R\text{—}COCl+SO_{2(g)}+HCl_{(g)} \quad (1)$$

Figure 4:
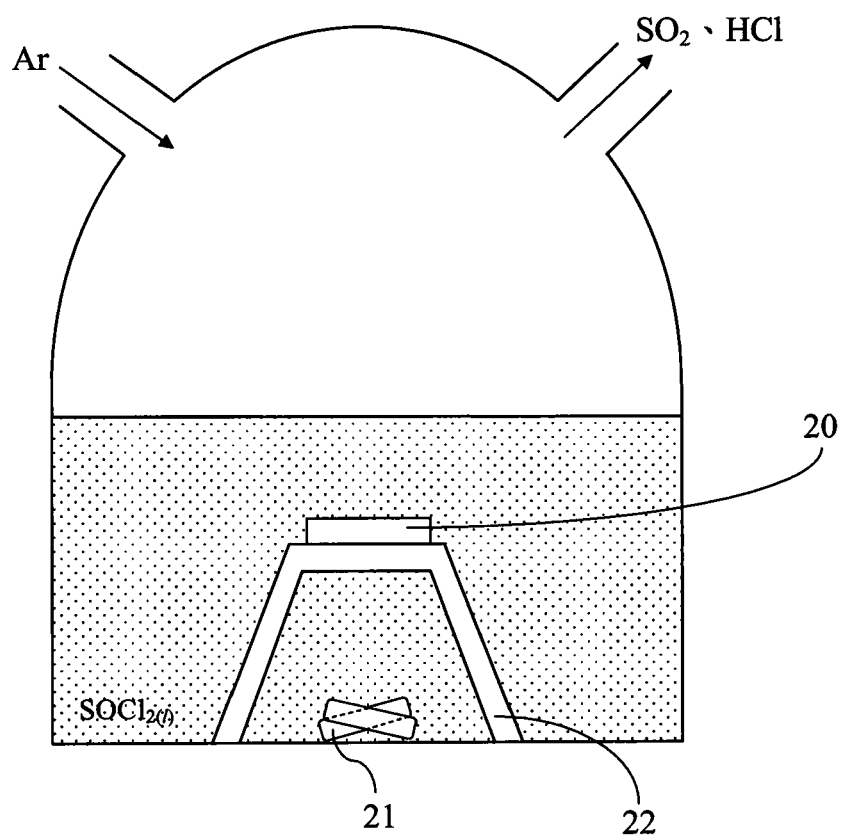
FIG. 4 is a diagram schematically a reflux system according to the present invention.

Refer to FIG. 4 a diagram schematically shows a reflux system. The microelectrode array 20 is immersed in the thionyl chloride solution, and an inert gas, such as argon, is pumped into the reflux system to implement the acyl-chlorination reaction. The product gases sulfur dioxide ($SO_2$) and hydrogen chloride (HCl) are taken away via a condensation tube. The acyl-chlorination process is undertaken at a temperature of 25-80° C. for 10-20 hours. A magnet 21 is placed on the bottom of the reflux system and used to agitate the solution to accelerate the reaction. The microelectrode array 20 is placed on a supporter 22, whereby the microelectrode array 20 is immersed in the thionyl chloride solution and exempted from the interference of the magnet 21. After the acyl-chlorination process, the microelectrode array 20 is dried for the succeeding treatment.

In the Step c, the acyl-chlorinated nanotubes are aminated, whereby the chlorine of the "O=C—Cl" functional groups are replaced by an amine to form an amine derivative having "O=C—~$NH_3^+$" functional groups at the terminals thereof, as shown in FIG. 3. The "O=C—~$NH_3^+$" functional group has very high affinity and excellent adherence to the neuron cells and is exempt from the adherence of glial cells. Therefore, the "O=C—~$NH_3^+$" functional groups can prevent from the glial cells aggregation and inhibit the formation of the sheaths, which will isolate the electrodes from the biological tissue and impair the signal measurement. The amine derivatives could be, but not limited to, 1,4-diaminobutane, ethylenediamine and EDC (1-ethyl-3-(3-dimethylaminopropyl) carbodiimide).

In one embodiment, the amination is realized with a chemical synthesis method, wherein the acyl-chlorinated carbon nanotubes react with 1,4-diaminobutane in a reflux system. The 1,4-diaminobutane is dissolved in a solvent by a concentration of 0.1-10 wt %. An appropriate amount of a basic compound is added into the solution to neutralize the acidity. The solvent is, but not limited to, toluene. Triethylamine may function as the basic compound to neutralize the acidic products of the reaction, but the basic compound is not limited to triethylamine. After the carbon nanotubes are modified by 1,4-diaminobutane, the chlorine atom is replaced by "—NH—$C_4$—$NH_3^+$", which has an amine functional group at the terminal thereof.

Figure 5A:
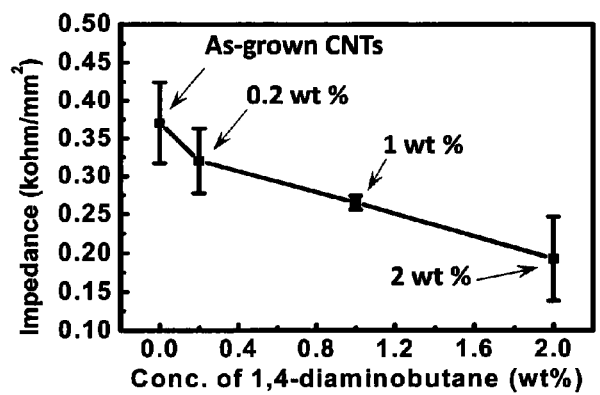
FIG. 5A is a diagram showing the impedance variation of a neural electrode before and after the modification of carbon nanotubes according to the present invention.
Figure 5B:
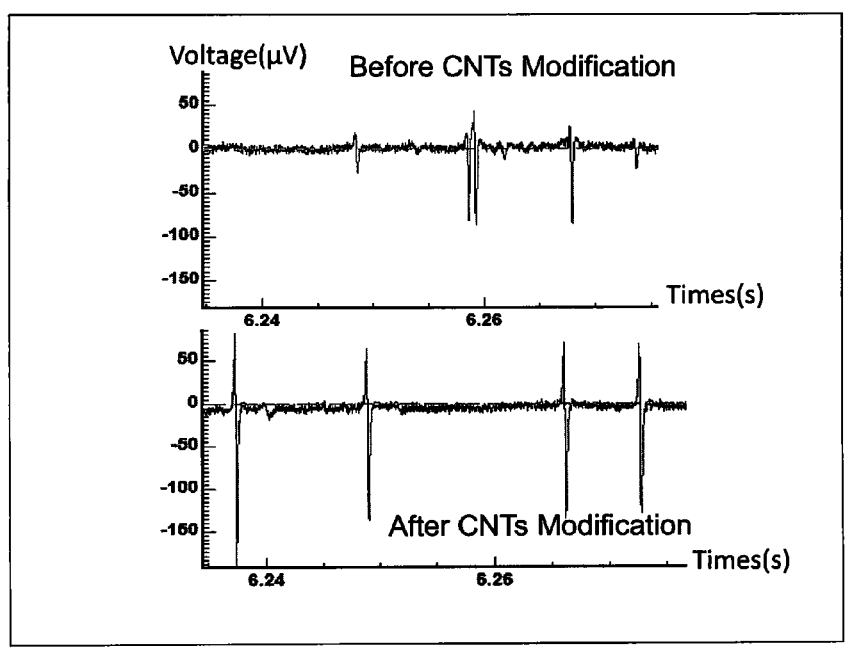
FIG. 5B is a diagram showing neural signals detected before and after the modification of carbon nanotubes according to the present invention.

Refer to FIG. 5A. The neural electrode containing the modified carbon nanotubes has lower impedance than the neural electrode containing the as-grown carbon nanotubes. In FIG. 5A, the horizontal axis represents the concentration of 1,4-diaminobutane in the Step c. With the increasing concentration of 1,4-diaminobutane, the amine functional groups also increase, and the impedance of the electrode decreases. Refer to FIG. 5B, after modifying the carbon nanotubes, the potential of the signals detected by the neural electrodes is much greater than before the modification. As shown in FIG. 5B, the electric potential and signal-to-noise ratio also increase after the modification.

In the abovementioned embodiments, what are modified are the carbon nanotubes that have been formed on the electrodes of a microelectrode array. However, the present invention also includes the case: independent carbon nanotubes are modified firstly, and the modified carbon nanotubes are formed on the neural electrodes via a coating method, a printing method, or another method.

The present invention also proposes a microelectrode array, which comprises a base and at least one probe connected to the base. Each probe has at least one electrode using the carbon nanotubes as the interface thereof. Each electrode is connected to the base via a wire. The carbon nanotubes are modified with the above-mentioned method to contain amine functional groups.

Figure 6:
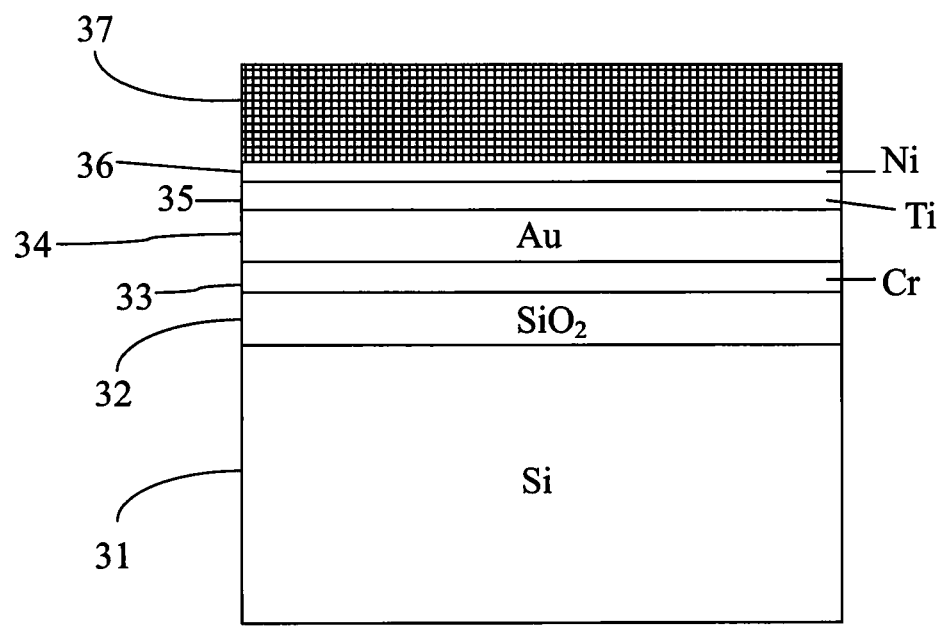
FIG. 6 is a cross-section view of a carbon nanotube electrode interface according to one embodiment of the present invention.

The microelectrode array of the present invention is fabricated from the combination of a silicon wafer and a complementary metal-oxide-semiconductor (CMOS) in the semiconductor processing techniques. Refer to FIG. 6 a sectional view schematically showing an electrode 30 using the carbon nanotubes as the interface thereof. The electrode 30 includes a carbon nanotube layer 37, a conductive layer 34 and a catalytic layer 36. The carbon nanotube layer 37 is the measurement interface of the electrode 30. The conductive layer 34 (such as a gold layer shown in FIG. 6) is deposited on a first adhesion layer 33 (such as a chromium layer shown in FIG. 6) and over the silicon wafer 31, and a position and dimensions of the electrode 30 are thus defined. In one embodiment, an insulating layer 32 (such as a silicon dioxide layer shown in FIG. 6) is formed between the conductive layer 34 and the wafer 31. The catalytic layer 36 is formed over the conductive layer 34, and the carbon nanotube layer 37 is catalytically formed on the catalytic layer 36. The catalytic layer 36 is made of iron, cobalt, or nickel. In FIG. 6, the catalytic layer 36 is a nickel layer having a thickness of about 5 nm. In one embodiment, the catalytic layer 36 is formed on a second adhesion layer 35 and over the conductive layer 34, and the second adhesion layer 35 is a titanium layer having a thickness of about 10-30 nm in FIG. 6. In one embodiment, the carbon nanotube layer 37 is synthesized at a temperature of 350-400° C.

In the present invention, the modified carbon nanotube interfaces of the electrodes of the microelectrode array can obviously increase the adherence of neuron cells to the electrodes. Thus, the microelectrode array can be implanted into the biological tissue to perform a long-time measurement. Further, the microelectrode array of the present invention can perform intracellular recording to obtain higher-intensity signals.

The embodiments described above are only to exemplify the present invention but not to limit the scope of the present invention. Any equivalent modification or variation according to the spirit of the present invention is to be also included within the scope of the present invention.

What is claimed is:

1. A method for modifying a carbon nanotube electrode interface, which modifies carbon nanotubes used as a neuron-electrode interface and comprises the steps of: performing a carboxylation process on the carbon nanotubes, performing an acyl-chlorination process on the carbon nanotubes, and performing an amination process on the carbon nanotubes, whereby surfaces of the carbon nanotubes have amine functional groups.

2. The method for modifying a carbon nanotube electrode interface according to claim 1, wherein the carboxylation process is a $H_2O$ plasma process.

3. The method for modifying a carbon nanotube electrode interface according to claim 2, wherein the $H_2O$ plasma process is performed at a temperature of 25-150° C., under a pressure of 1-100 Torr, with a power of 25-100 W, for 10-300 seconds.

4. The method for modifying a carbon nanotube electrode interface according to claim 1, wherein in the acyl-chlorination process, the carbon nanotubes react with thionyl chloride in a reflux system.

5. The method for modifying a carbon nanotube electrode interface according to claim 4, wherein a microelectrode array using the carbon nanotubes as the neuron-electrode interface thereof is placed in the reflux system for a reaction, and wherein the microelectrode array is placed on a carrier lest a magnet of the reflux system interfere with the reaction.

6. The method for modifying a carbon nanotube electrode interface according to claim 4, wherein the acyl-chlorination process is performed at a temperature of 25-80° C. for 10-20 hours.

7. The method for modifying a carbon nanotube electrode interface according to claim 1, wherein in the amination process, the carbon nanotubes react with a compound selected from a group consisting of 1,4-diaminobutane, ethylenediamine, and EDC (1-ethyl-3-(3-dimethylaminopropyl)carbodiimide).

8. A microelectrode array comprising a base and at least one probe connected to the base, wherein each the probe has at least one electrode using carbon nanotubes as an interface thereof, and wherein each the electrode is connected to the base via a wire, and wherein the carbon nanotubes are modified to contain amine functional groups according to any of claim 1.

9. The microelectrode array according to claim 8, wherein the electrode includes a conductive layer and a catalytic layer, and wherein the conductive layer is formed over a silicon wafer to define a position and dimensions of the electrode, and wherein the carbon nanotubes are catalyzed by the catalytic layer to form on the catalytic layer.

10. The microelectrode array according to claim 9, wherein the catalytic layer is made of a material selected from a group consisting of iron, cobalt, and nickel.

* * * * *